United States Patent
Palti

(10) Patent No.: US 11,020,095 B2
(45) Date of Patent: Jun. 1, 2021

(54) DATA COMPRESSION TO FACILITATE REMOTE MEDICAL ANALYSIS AND DIAGNOSIS

(71) Applicant: Yoram Palti, Haifa (IL)

(72) Inventor: Yoram Palti, Haifa (IL)

(73) Assignee: Echosense Jersey Limited, St. Helier (JE)

( * ) Notice: Subject to any disclaimer, the term of this patent is extended or adjusted under 35 U.S.C. 154(b) by 1065 days.

(21) Appl. No.: 15/434,998

(22) Filed: Feb. 16, 2017

(65) Prior Publication Data

US 2017/0156707 A1 Jun. 8, 2017

Related U.S. Application Data

(63) Continuation-in-part of application No. 14/994,089, filed on Jan. 12, 2016.

(Continued)

(51) Int. Cl.
*A61B 8/08* (2006.01)
*A61B 8/00* (2006.01)
(Continued)

(52) U.S. Cl.
CPC .......... *A61B 8/5223* (2013.01); *A61B 5/0002* (2013.01); *A61B 5/7232* (2013.01);
(Continued)

(58) Field of Classification Search
CPC .......... A61B 8/02; A61B 8/04; A61B 8/0883; A61B 8/4236; A61B 8/4455; A61B 8/485;
(Continued)

(56) References Cited

U.S. PATENT DOCUMENTS

| | | | | |
|---|---|---|---|---|
| 4,770,184 A | * | 9/1988 | Greene, Jr. .......... | A61B 5/7257 600/454 |
| 5,360,005 A | | 11/1994 | Wilk | |

(Continued)

FOREIGN PATENT DOCUMENTS

JP       2010083205 A      4/2010

OTHER PUBLICATIONS

Palodeto et al., "Methodology for Classification and Analysis of Neonate and Adult ECG," Proceedings of the IFMBE World Congress on Medical Physics and Biomedical Engineering, vol. 14/2, pp. 1214-1217, 2006.

(Continued)

*Primary Examiner* — Amelie R Davis
(74) *Attorney, Agent, or Firm* — Potomac Law Group, PLLC

(57) ABSTRACT

Cardiac monitoring is implemented by transmitting ultrasound energy into a lung of the subject, receiving ultrasound reflections, detecting Doppler shifts in the received reflections, and processing the Doppler shifts into power and velocity data. A plurality of cardiac cycles are identified within the power and velocity data, and a plurality of features corresponding to each of the plurality of cardiac cycles are identified. The identified features are characterized into a set of parameters, and the set of parameters is transmitted to a remote location. The set of parameters is analyzed at the remote location to determine if an abnormality exists. If an abnormality exists, an indication is output from the remote location.

14 Claims, 11 Drawing Sheets

Related U.S. Application Data

(60) Provisional application No. 62/296,255, filed on Feb. 17, 2016, provisional application No. 62/103,633, filed on Jan. 15, 2015.

(51) Int. Cl.
  *A61B 8/02* (2006.01)
  *A61B 5/00* (2006.01)
  *A61B 8/04* (2006.01)

(52) U.S. Cl.
  CPC .............. *A61B 8/02* (2013.01); *A61B 8/0883* (2013.01); *A61B 8/4236* (2013.01); *A61B 8/488* (2013.01); *A61B 8/5284* (2013.01); *A61B 8/04* (2013.01); *A61B 8/4455* (2013.01); *A61B 8/485* (2013.01); *A61B 8/543* (2013.01); *A61B 8/565* (2013.01)

(58) Field of Classification Search
  CPC ..... A61B 8/488; A61B 8/5223; A61B 8/5284; A61B 8/543; A61B 8/565; A61B 5/7232
  See application file for complete search history.

(56) References Cited

U.S. PATENT DOCUMENTS

| | | | |
|---|---|---|---|
| 5,467,779 A | 11/1995 | Smith et al. | |
| 5,598,845 A | 2/1997 | Chandraratna et al. | |
| 6,629,937 B2 | 10/2003 | Watrous | |
| 7,844,331 B2 | 11/2010 | Li et al. | |
| 8,968,203 B2 | 3/2015 | Palti | |
| 8,992,428 B2 | 3/2015 | Palti | |
| 9,357,939 B1 | 6/2016 | Nosrati | |
| 9,750,431 B2 | 9/2017 | Palti | |
| 2007/0142866 A1 | 6/2007 | Li et al. | |
| 2008/0058661 A1 | 3/2008 | Bardy | |
| 2008/0214946 A1 | 9/2008 | Miller et al. | |
| 2008/0312543 A1* | 12/2008 | Laufer | A61B 5/0215 600/486 |
| 2010/0274133 A1* | 10/2010 | Palti | A61B 8/5223 600/454 |
| 2011/0125023 A1 | 5/2011 | Palti et al. | |
| 2012/0197128 A1 | 8/2012 | Palti | |
| 2014/0039313 A1 | 2/2014 | Palti | |
| 2014/0058280 A1* | 2/2014 | Chefles | G06F 19/3418 600/521 |
| 2015/0051500 A1* | 2/2015 | Elliott | A61B 5/0261 600/480 |

OTHER PUBLICATIONS

International Search Report and Written Opinion for International Application No. PCT/IB2016/050148, dated May 23, 2016.

Palti et al., "Footprints of Cardiac Mechanical Activity as Expressed in Lung Doppler Signals," Echocardiography (2015):407-410.

Palti et al., "Pulmonary Doppler signals: a potentially new diagnostic tool," European Journal of Echocardiography, vol. 12, No. 12, pp. 940-944, Oct. 2011.

Goldwasser et al., "A new method of filtering T Waves to detect hidden P waves in electrocardiogram signals," Europace, vol. 13, pp. 1028-1033, 2011.

* cited by examiner

DATA COMPRESSION TO FACILITATE REMOTE MEDICAL ANALYSIS AND DIAGNOSIS

CROSS REFERENCE TO RELATED APPLICATIONS

This application claims the benefit of U.S. Provisional Application 62/296,255, filed Feb. 17, 2016; and this application is also a continuation-in-part of U.S. application Ser. No. 14/994,089, filed Jan. 12, 2016, which claims the benefit of U.S. Provisional Application 62/103,633, filed Jan. 15, 2015. Each of the above-identified applications is incorporated herein by reference in its entirety.

BACKGROUND

This application relates to a system designed to provide medical services with a device used in a clinic or a patient's home.

SUMMARY OF THE INVENTION

One aspect of the invention is directed to a first method for analyzing health of a subject. This method includes the steps of transmitting ultrasound energy into a lung of the subject, receiving ultrasound energy reflected from the lung of the subject and detecting Doppler shifts in the received reflections, and processing the Doppler shifts into power and velocity data. This method also includes the steps of identifying a plurality of cardiac cycles within the power and velocity data and identifying a plurality of features of the power and velocity data corresponding to each of the plurality of cardiac cycles. The extraction of features may be based on anatomical, physiological and/or pathological models. This method also includes the steps of characterizing each of the identified features into a set of parameters and transmitting the set of parameters for each of the identified features to a remote location. The set of parameters for each of the identified features for each of the plurality of cardiac cycles is analyzed at the remote location to determine if an abnormality exists in at least one of the plurality of cardiac cycles. If it is determined in this analyzing that an abnormality exists in at least one of the plurality of cardiac cycles, an indication from the remote location that the abnormality exists is output.

In some embodiments of the first method, the step of processing the Doppler shifts into power and velocity data includes an algorithm designed to increase signal from moving borders between blood vessels in the lung and air filled alveoli that surround the blood vessels, with respect to other reflected ultrasound signals.

In some embodiments of the first method, the step of identifying cardiac cycles comprises the steps of determining an envelope of the power and velocity data and identifying cardiac cycles based on the determined envelope.

In some embodiments of the first method, the set of parameters for each of the identified features comprises at least two of: a power integral, duration, peak velocity, a timing of peak velocity, peak power, a timing of peak power, average velocity, average power, rising slope of a velocity curve, rising slope of a power curve, falling slope of a velocity curve, falling slope of a power curve. In some embodiments of the first method, the set of parameters for each of the identified features comprises at least peak velocity and a timing of peak velocity.

In some embodiments of the first method, the indication from the remote location that the abnormality exists specifies a nature of the abnormality.

In some embodiments of the first method, the step of analyzing the set of parameters comprises detecting when (a) a peak velocity of a systolic feature is lower than expected for healthy subjects, (b) the peak velocity of the systolic feature arrives later than expected for healthy subjects, (c) a peak velocity of an atrial feature is lower than expected for healthy subjects, and (d) the peak velocity of the atrial feature arrives later than expected for healthy subjects. In these embodiments, the indication from the remote location that the abnormality exists specifies that the abnormality is pulmonary hypertension.

In some embodiments of the first method, the step of analyzing the set of parameters comprises detecting when an extra systolic feature, an extra diastolic feature, and an extra atrial feature appear within a given cardiac cycle. In these embodiments, the indication from the remote location that the abnormality exists specifies that the abnormality is atrial extra systole of sinus origin.

In some embodiments of the first method, the step of analyzing the set of parameters comprises detecting when a plurality of extra atrial features appears within a given cardiac cycle. In these embodiments, the indication from the remote location that the abnormality exists specifies that the abnormality is atrial flutter.

In some embodiments of the first method, the step of analyzing the set of parameters comprises detecting when an atrial feature is missing from a given cardiac cycle. In these embodiments, the indication from the remote location that the abnormality exists specifies that the abnormality is atrial fibrillation.

In some embodiments of the first method, the step of analyzing comprises performing classification using a support vector machine.

In some embodiments of the first method, the step of transmitting the set of parameters for each of the identified features to a remote location comprises transmitting data via the Internet. In some embodiments of the first method, the step of transmitting the set of parameters for each of the identified features to a remote location comprises transmitting data via a telephone network.

Another aspect of the invention is directed to a second method for analyzing health of a subject. This method includes the steps of transmitting ultrasound energy into a lung of the subject, receiving ultrasound energy reflected from the lung of the subject and detecting Doppler shifts in the received reflections, and processing the Doppler shifts into power and velocity data. This method also includes the steps of identifying a plurality of cardiac cycles within the power and velocity data and identifying a plurality of features of the power and velocity data corresponding to each of the plurality of cardiac cycles. The extraction of features may be based on anatomical, physiological and/or pathological models. This method also includes the steps of characterizing each of the identified features into a set of parameters and analyzing the set of parameters for each of the identified features for each of the plurality of cardiac cycles to determine if an abnormality exists in at least one of the plurality of cardiac cycles. If it is determined in this analysis step that an abnormality exists in at least one of the plurality of cardiac cycles, an indication that the abnormality exists is output.

In some embodiments of the second method, the step of processing the Doppler shifts into power and velocity data includes an algorithm designed to increase signal from moving borders between blood vessels in the lung and air filled alveoli that surround the blood vessels, with respect to other reflected ultrasound signals.

In some embodiments of the second method, the step of identifying cardiac cycles comprises the steps of determining an envelope of the power and velocity data and identifying cardiac cycles based on the determined envelope.

In some embodiments of the second method, the set of parameters for each of the identified features comprises at least two of: a power integral, duration, peak velocity, a timing of peak velocity, peak power, a timing of peak power, average velocity, average power, rising slope of a velocity curve, rising slope of a power curve, falling slope of a velocity curve, falling slope of a power curve. In some embodiments of the second method, the set of parameters for each of the identified features comprises at least peak velocity and a timing of peak velocity.

In some embodiments of the second method, the indication that the abnormality exists specifies a nature of the abnormality.

Another aspect of the invention is directed to a system for analyzing health of a subject. This system includes an ultrasound transducer located at a first location and configured to transmit ultrasound energy into a lung of the subject and receive ultrasound energy reflected from the lung of the subject, and an ultrasound processor located at the first location and configured to detect Doppler shifts in the received reflections and process the Doppler shifts into power and velocity data. This system also includes a first processor located at the first location and configured to identify a plurality of cardiac cycles within the power and velocity data, identify a plurality of features of the power and velocity data corresponding to each of the plurality of cardiac cycles, characterize each of the identified features into a set of parameters, and transmit the set of parameters for each of the identified features to a second location that is remote from the first location. The extraction of features may be based on anatomical, physiological and/or pathological models. This system also includes a second processor located at the second location. The second processor is configured to (a) analyze the set of parameters for each of the identified features for each of the plurality of cardiac cycles to determine if an abnormality exists in at least one of the plurality of cardiac cycles, and, (b) if it is determined that an abnormality exists in at least one of the plurality of cardiac cycles, output an indication that the abnormality exists.

DESCRIPTION OF THE PREFERRED EMBODIMENTS

Data is acquired from the patient using one or more sensors in a clinic or in the patient's home. Examples of data that may be acquired includes echo sonogram data, X-ray image data, MRI data, etc. This data is preprocessed locally by a data reduction processor to dramatically reduce the volume of data. This reduced-volume data is then transmitted to the server together with the relevant clinical information.

The server receives the data and processes it to evaluate a condition of the patient. The data processing implemented at the server may include classification, diagnosis, etc., and it may be based on algorithms and/or additional data about the patient that is either input or previously stored on the server. After the server processes the data, the relevant processed information and conclusions are transmitted back to the clinic, health care provider, or directly to the patient. Optionally, the server may provide recommendations as to treatment, need for hospitalization, etc. to the relevant individual or entity.

Figure 1:
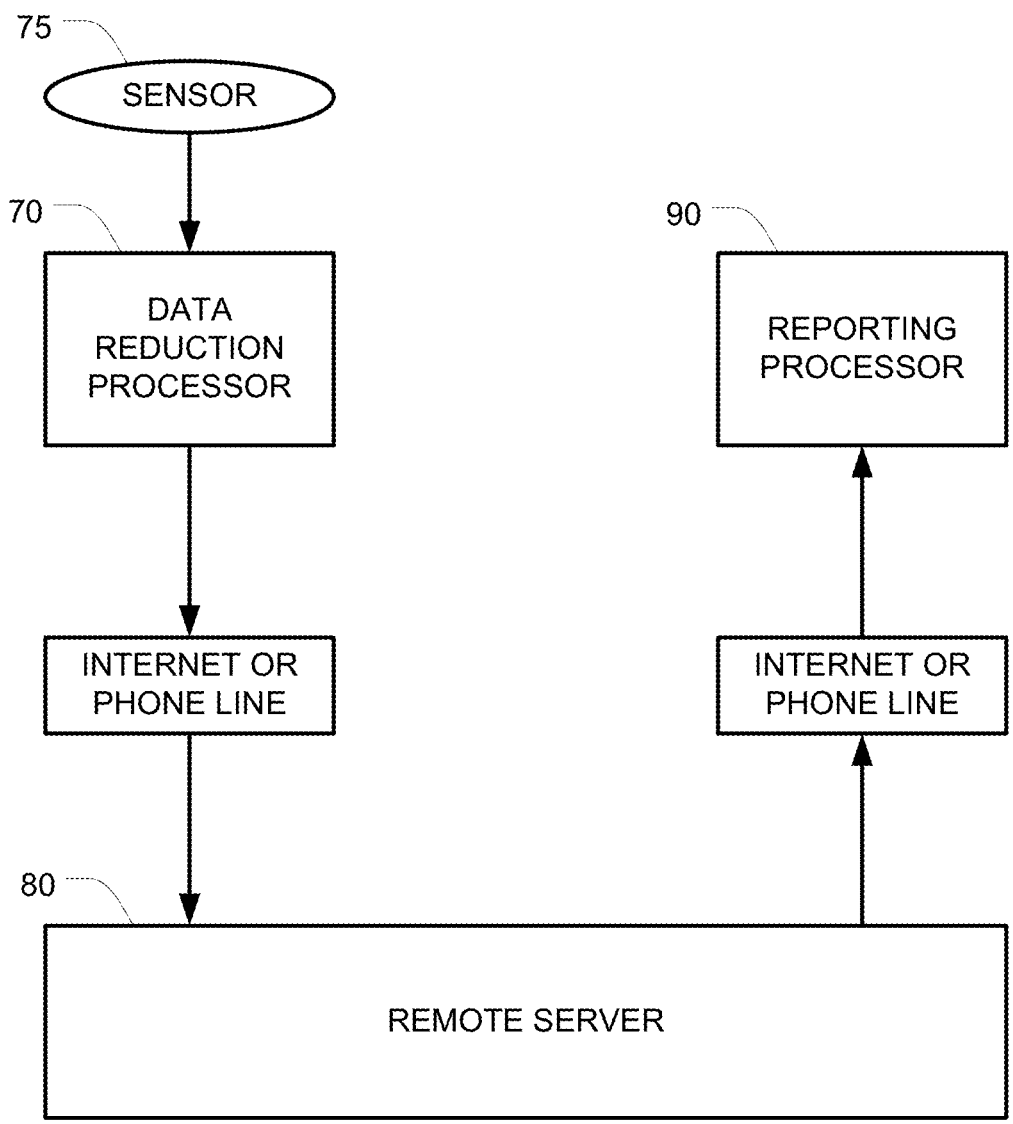
FIG. 1 is a block diagram of a preferred embodiment that includes a set of components located in the vicinity of the patient and a remote server.

FIG. 1 is a block diagram of a preferred embodiment. In this embodiment, the sensor 75 and the data reduction processor 70 are located in the vicinity of the patient (e.g., at the clinical site or the patient's home). These components make up the On-Site Device ("OSD"), which preferably includes the following components/functions: (1) One or more sensors and operating systems for acquiring the relevant information from the patient, such as an ultrasound probe, electrodes, X-ray machine, gamma source and camera, etc.; (2) a suitable front end that depends on the type of sensor (e.g., data input amplifiers, analog-to digital converter, filters, etc., which are used to operate the sensor and receive data that the sensor generates; (3) data storage; (4)

data processing, compression data coding, etc.; and (5) a communication system for transmitting data to the server 80 and receiving results from the server. Preferably, these transmissions are encrypted.

The server 80 receives the data that was acquired by the OSD and processed in the OSD to reduce the volume of data. The server 80 may be located at a physical facility that is remote from the patient (i.e., not in the same building as the patient) or it may be hosted in the cloud. Advantages of implementing the server in the cloud include the availability of large amounts of computation power and communication capabilities. The server 80 server preferably includes the following components/functions: (1) a communication system for receiving the data that was transmitted by the OSD and forwarding the analysis diagnosis and other information to the relevant sites; (2) data processing capacity such as deciphering the data, and/or classification using a classification program and algorithms designed for the appropriate physio-pathological model; (3) determining the diagnosis and sending a response to the OSD or other suitable site, (4) preparing a corresponding invoice and transmitting the invoice to the appropriate party. Preferably, the transmissions from the server 80 are encrypted.

Note that unlike conventional compression techniques (in which the goal is to deliver either an exact copy of an original signal or an approximation of the original signal to the destination), the compression that is implemented in the preferred embodiments does not attempt to deliver an approximation of the original data to a destination. Instead, the OSD extracts the relevant features from the data that was captured by the sensor, and transmits characterizations of those extracted features to the server 80. The characterizations of the extracted features are selected so that even though the server 80 does not have access to the original data that was sensed by the sensor, the server 80 will have enough information to make a meaningful analysis of the patient's condition. This type of compression is referred to herein as Data Physio-Pathol Compression or DPPC. The aim of the DPPC is to extract the relevant features that are necessary to recognize and characterize a condition, and transmit only that data to the remote server 80 which will, in turn, diagnose the disease, etc. This configuration advantageously eliminates the need to transmit massive quantities of data to the remote server 80. It also eliminates the need to maintain large amounts of processing power at each OSD, and makes it more difficult for hackers to access the algorithms that are used to make the diagnosis.

In some embodiments, two or more DPPC's may be used, each relating to different physiology and pathology of some body system of interest (for example the cardio-vascular system) or a specific organ/tissue such as the heart, lung, muscle, etc. Furthermore, the features may be specific to a certain measurement modality or to a combination thereof, as made of an organ/tissue, for example ultrasound images, ultrasound Doppler coupled with electric ECG measurement and pressure measurement, X-ray, MRI, blood pressure, blood composition, etc.

In some instances, the original data volume that was captured by the sensor may be in the range of 10-100 Mbyte. Preferably, after DPPC is implemented, the data volume that must be transmitted is reduced to the range of 1 Kbyte.

Example 1

A first example shows how the system can be used to detect the condition of a patient's heart based on Doppler ultrasound sonograms obtained from the patient's lungs. The inventor has found that transthoracic Doppler aimed at the lungs can detect signals that reflect cardiac activity, as described in Y. Palti et al., Pulmonary Doppler Signals: A Potentially New Diagnostic Tool, Eur J Echocardiography 12; 940-944 (2011); and Y. Palti et al., Footprints of Cardiac Mechanical Activity as Expressed in Lung Doppler Signals, Echocardiography 32(3):407-410 (2015). Doppler signals obtained from a human lung are referred to herein as Lung Doppler Signals, or LDS, and they are in synchrony with the cardiac cycle. An explanation of LDS is provided in U.S. patent application Ser. No. 12/912,988 (filed Oct. 27, 2010), which is incorporated herein by reference in its entirety. That application (which was published as US2011/0125023) describes detecting Doppler shifts of reflected ultrasound induced by moving borders between blood vessels in the lung and air filled alveoli that surround the blood vessels, and that the movement of the border is caused by pressure waves in the blood vessels that result in changes in diameter of those blood vessels. That application also describes approaches for processing the detected Doppler shifts with an algorithm designed to increase signal from the moving border with respect to other reflected ultrasound signals.

Doppler ultrasound is used to determine the power at every relevant velocity in a target region of the subject, over time. This is accomplished by generating pulsed ultrasound beams, picking up the reflected energy, calculating the Doppler shifts as well as phase shifts, and processing the data thus obtained to provide the matrix of power and corresponding velocities of the ultrasound reflectors.

The sensors for obtaining LDS are similar to conventional Trans Cranial Doppler (TCD) systems in that the ultrasound beam is directly aimed at the known location of the target, without relying on imaging. And because the lungs are so large, aiming at the relevant anatomy is much easier than in the TCD context. The front end and data acquisition portion of the embodiments described herein are preferably configured similarly to a conventional TCD pulsed Doppler systems. Examples of such a system are the Sonara/tek pulsed Trans-Cranial-Doppler device and TPD. Note that in the Sonara/tek system, the acquired data is sent to an external computer that is loaded with software to generate a conventional Doppler ultrasound display (e.g., on a monitor associated with the computer) in which the x axis represents time, the y axis represents velocity, and power is represented by color. But the functionality of this external computer and display is not necessary in the embodiments described herein.

This embodiment is similar to TPD system, described in the two references identified above, because it preferably uses a relatively wide beam. For example, beams with an effective cross section of at least ½ cm are preferred (e.g., between ½ and 3 cm) may be used. This may be accomplished by using a smaller transducer, and by using single element transducers instead of phased array transducers that are popular in other anatomical applications. When a wider beam is used, the system can take advantage of the fact that the lungs contain relatively large complexes of unspecified geometrical shape consisting of blood vessels (both arteries and veins) and their surrounding lung tissues, and focusing becomes less critical. For example, the same transducers that are used in standard TCD probes (like those available for use with the Sonara/tek machine) may be used, such as a 21 mm diameter, 2 MHz sensor with a focal length of 4 cm. Another example, the transducer may be implemented using a thin ceramic patch of piezoelectric material.

Note that since imaging the lung with ultrasound is impossible because of the scattering, one has to scan for targets without guidelines, except for the known anatomy. But this is not problematic because LDS can be obtained from any territory of the lungs, and the lungs are large and have a known location. PW (pulsed wave) Doppler ultrasound with relatively wide beams may be used.

Figure 2:
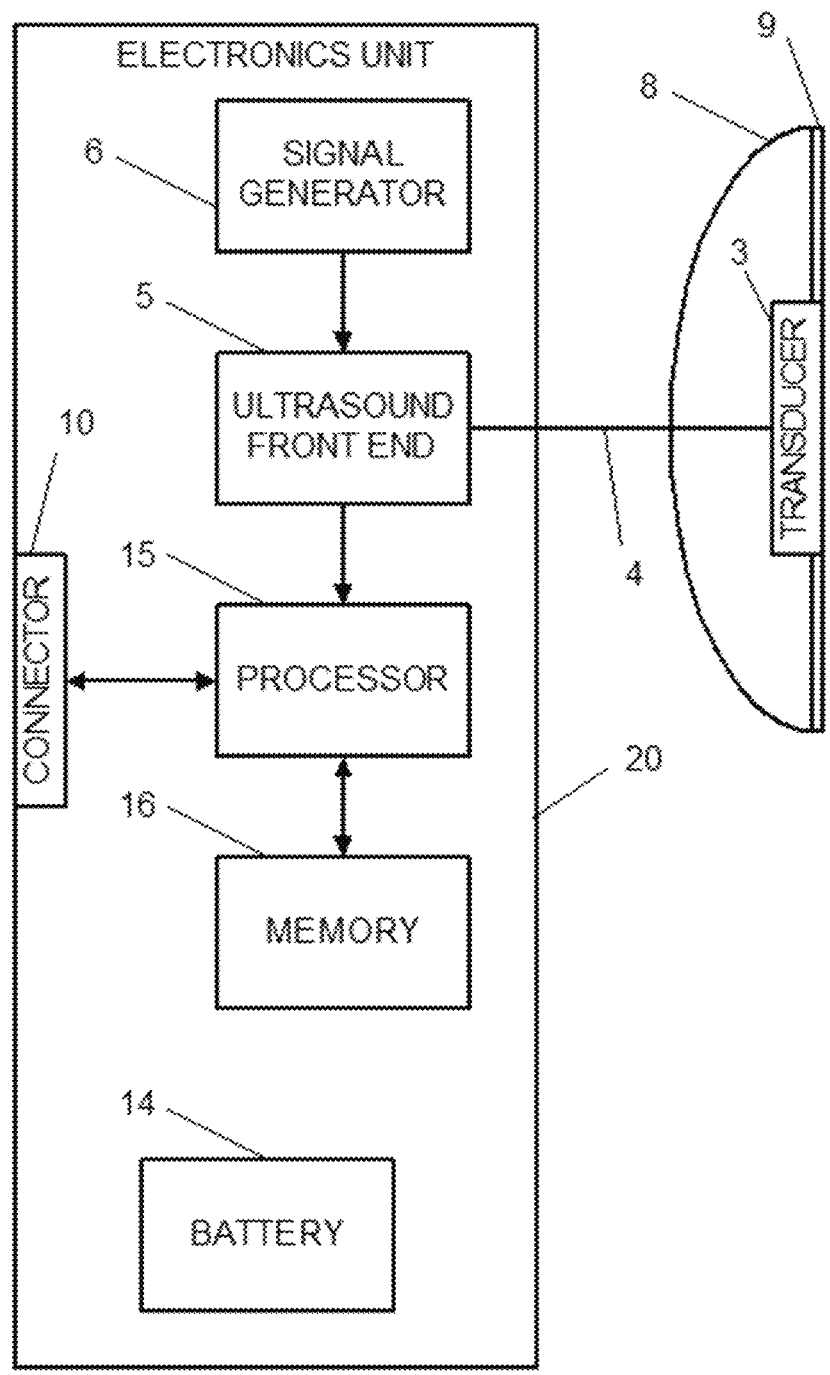
FIG. 2 depicts a first embodiment for implementing the portion of the system located in the vicinity of the patient in the FIG. 1 embodiment

FIG. 2 depicts a first embodiment for implementing the OSD portion of the system in this embodiment. The OSD contains an electronics unit 20 and a transducer 3. The transducer 3 is preferably made from a thin flat piezoelectric element 2 (e.g., between 0.1-1 mm thick) such as a ceramic disk, with a diameter preferably in the range of 0.5-5 cm, or between 1 and 3 cm. The transducer 3 is preferably encapsulated within a biocompatible electrically insulated casing 8 that is fixed to the chest wall using an appropriate adhesive 9 similar to the adhesives used for ECG electrode. Taken together, the transducer 3 in the casing 8 resembles a patch. The transducer 3 is connected to the electronics unit 20 via a cable that contains the leads 4. In some embodiments, the electronics unit 20 may be miniaturized and incorporated in the same housing as the transducer 3.

The electronics unit 20 includes a signal generator 6 that generates appropriate signals for driving the ultrasound transducer. Suitable signals include pulsed AC signals ranging from 1-4 MHz. In some preferred embodiments, pulsed AC signals with a frequency of about 2 MHz is used. The signal from the signal generator 6 is amplified and sent to the transducer 3 via the ultrasound front end 5, and the amplified signal is delivered to the transducer 3 via the leads 4, to excite the transducer. A suitable pulse duration for use this embodiment will typically be 2-10 microseconds (more preferably 2-5 μSec), with a repetition rate 100-3000 Hz, (more preferably 100-1000 Hz). This repetition rate is sufficiently high to be consistent with the Nyquist criterion rate for measuring Doppler shifts corresponding to velocities of 10-15 cm/sec, or potentially up to about 50 cm/sec.

The ultrasound waves reflected back from body reflectors that are moving relative to the transducer 3 are picked up by the transducer 3. They are amplified and digitized in the ultrasound front end 5 and converted into power and velocity data in a conventional manner. The power and velocity data is delivered to the processor 15, which is programmed to implement a first set of algorithms described below. A second set of algorithms is subsequently implemented in the remote server 80. The processor has access to memory 16 for storing any data that will ultimately be delivered to the server 80. The data stored in memory 16 can be delivered to the server 80 via a wired connection via connector 10, and/or via a wireless connection (e.g., Bluetooth).

Figure 3A:
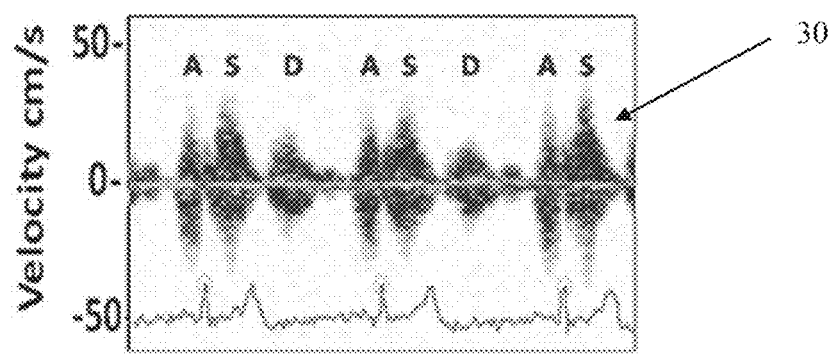
FIG. 3A depicts a set of LDS signals for a person with a normal heartbeat.
Figure 3B:
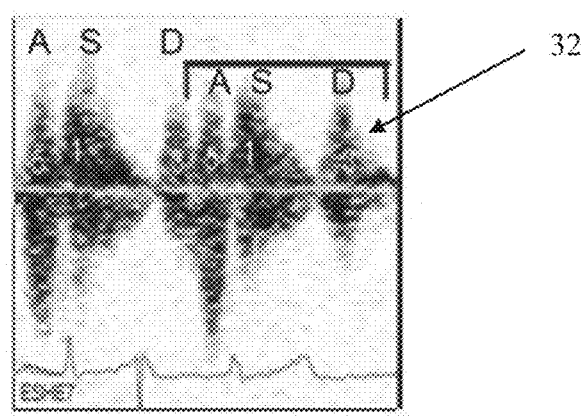
FIG. 3B depicts a set of LDS signals for heartbeats with an atrial extra systole.
Figure 3C:
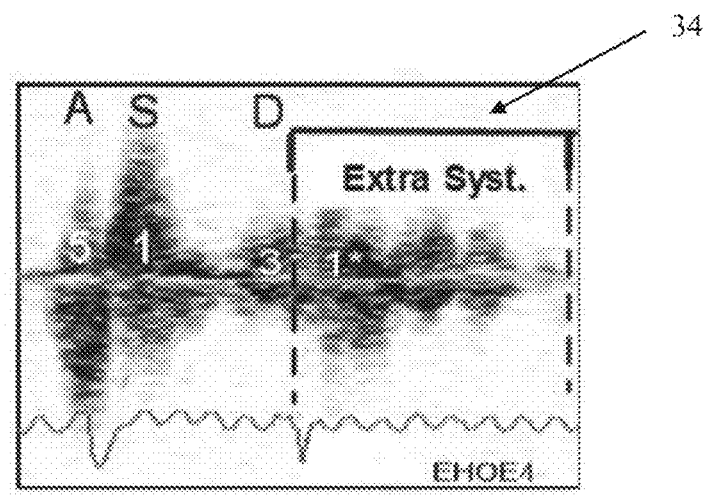
FIG. 3C depicts a set of LDS signals for heartbeats with a ventricular extra systole.
Figure 3D:
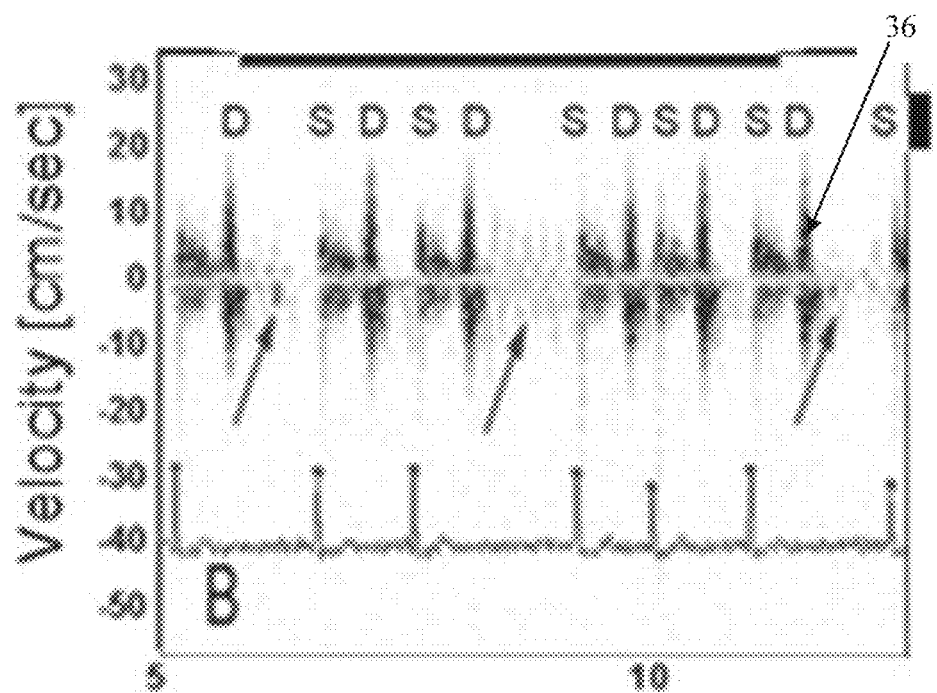
FIG. 3D depicts a set of LDS signals for heartbeats with atrial fibrillation.
Figure 3E:
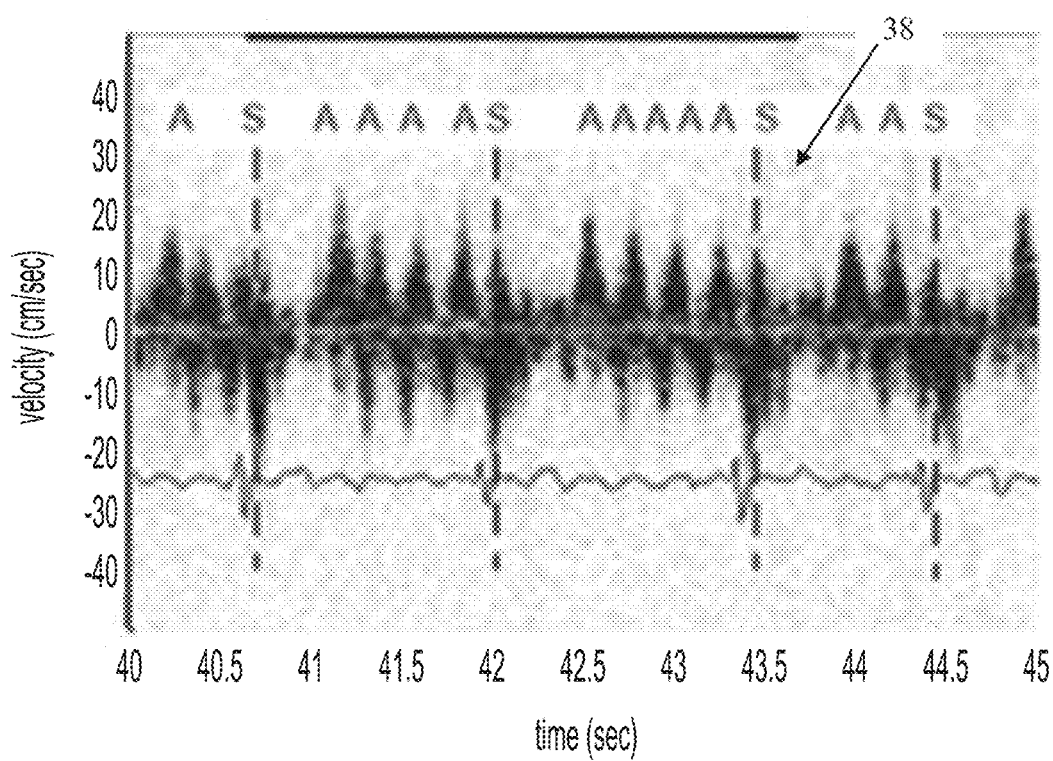
FIG. 3E depicts a set of LDS signals for heartbeats with atrial flutter.

FIGS. 3A-3F are included to describe the theory of operation of the embodiments described herein. But it is important to note that the displays depicted in those figures are not actually generated by the OSD 70. Instead, these figures depict the displays would be obtained if the LDS power and velocity data obtained by the OSD were processed into a conventional Doppler ultrasound display in which the x axis represents time, the y axis represents velocity, and power is represented by color. (Note that in the figures, the conventional color display is replaced by grayscale for purposes of filing in this patent application.) Five different scenarios are depicted in FIGS. 3A-3F: normal heartbeats (FIG. 3A); heartbeats with an atrial extra systole (FIG. 3B); heartbeats with a ventricular extra systole (FIG. 3C); heartbeats with atrial fibrillation (FIG. 3D); and heartbeats with atrial flutter (FIG. 3E).

It has been postulated that the LDS represent movements generated by the cardiac mechanical activity that propagate through the lung along its vascular system. The Doppler system measures the movement velocity by the frequency shifts as well as the changes in the reflected ultrasound power amplitude. These reflected ultrasound waves, as picked up by the system over the lung, are in the order of 80-100 dB, i.e. much stronger than the flow signals picked up by the standard Doppler systems from flow in blood vessels. This fact makes it possible to use the described simple patch transducers that rely on a single piezoelectric element, without the need for incorporating any focusing technology (e.g., by using a phased array transducer) into the system.

FIG. 3A shows that the LDS 30 for a normal heartbeat includes at least three distinct elements labeled S, D and A. These elements represent the mechanical movements associated with cardiac systole, diastole, and atrial contraction respectively. FIG. 3A also includes a conventional ECG trace (near the bottom) to illustrate the correlation between the various features (i.e., S, D, and A) of the LDS and the various features (e.g., an R wave) of the ECG.

FIG. 3B shows how the LDS 32 for heartbeats with an atrial extra systole of sinus origin are registered and how they can be clearly identified by their distinct structure. More specifically, an additional full three element signal 32 (A+D+S) appears at some point during a normal cycle, interrupting the normal cycle.

FIG. 3C shows how the LDS 34 for heartbeats with a ventricular extra systole are registered. More specifically, an odd shaped long duration single element 34 interposes the normal sequence of events.

FIG. 3D depicts LDS tracings 36 recorded from a patient with Atrial Fibrillation (AF). This recording shows clear S and D signals. But the presystolic signal (labeled A in the normal tracing seen in FIG. 3A) is missing when AF occurs, as seen in FIG. 3D. The presence of this pattern 36 (i.e., the missing "A" signal) in the LDS recording makes it possible to detection AF by analyzing the LDS, and an algorithm for detecting this situation is described below.

Figure 4:
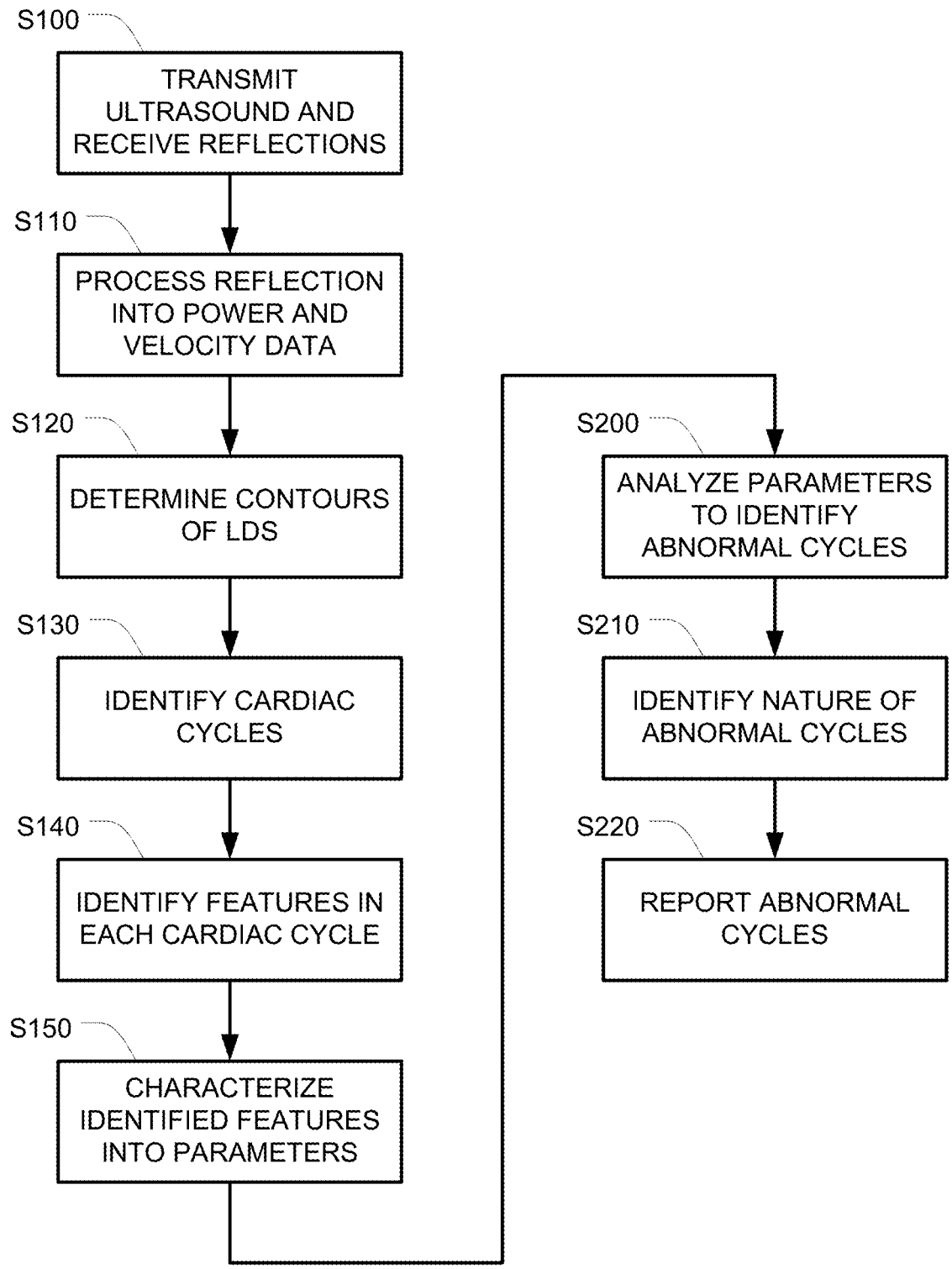
FIG. 4 is a flowchart of a data handling procedure that is implemented by the local data reduction processor and the remote server of the FIG. 1 embodiment.

FIG. 3E depicts LDS tracings 38 recorded and from a patient with Atrial Flutter (AFT). This recording shows a large number of extra "A" artifacts 38. The presence of this pattern in the LDS recording makes it possible to detection AFT by analyzing the LDS FIG. 4 is a schematic representation of the basic data handling procedure that is implemented by the data reduction processor 70 and the remote server 80 (both shown in FIG. 1), and details of the various steps depicted in FIG. 4 are described below. Notably, the processing is divided between the OSD 70 and the server 80. More specifically, steps S100-S150 are implemented in the OSD 70, and steps S200-S220 are implemented in the server 80.

In step S100, ultrasound energy is transmitted into the patient's lungs, and the reflected ultrasound energy is received, in a conventional manner (e.g., as described in the references identified above). In step S110, Doppler shifts in the received reflections are detected and processed into power and velocity data in a conventional manner, similar to the processing for conventional Doppler Sonograms. Note that because the Doppler returns from different positions on the patient's chest are similar, the placement of the transducer in an exact spot on the patient's chest in not necessary.

Conventional Doppler systems collect power and velocity data from many different depths or gates (e.g., 16 gates). But because the returns from different depths within the patient's lungs are roughly similar, the system does not have to collect the Doppler data from multiple gates. Instead, the data from a single gate can be used for all subsequent processing described herein. This results in a significant decrease in the amount of data that must be processed. Optionally, the optimal gate or gates can be determined by analyzing the sonograms obtained from a few depths. Subsequently to this determination only the selected gate data will be used.

Figure 5:
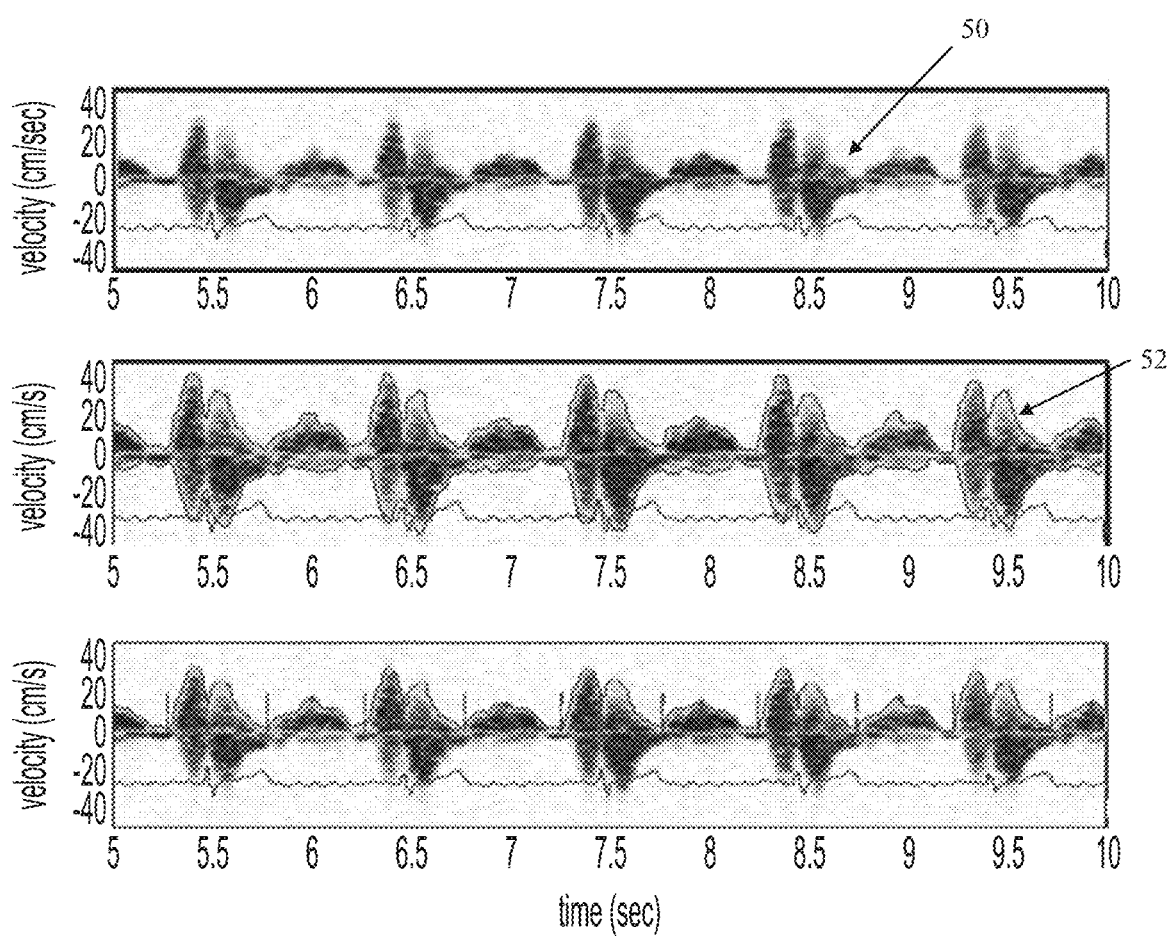
FIG. 5 depicts an example of LDS power and velocity data for a series of four heartbeats.

In step S120, the contours (i.e., envelope) of the LDS power and velocity data is determined using any conventional envelope-detecting algorithm. The top panel of FIG. 5 is an example of LDS power and velocity data 50 for a series of four heartbeats. And the trace 52 in the middle panel of FIG. 5 shows the contour (i.e., the envelope) of that LDS data. (Note once again that displays depicted in FIG. 5 are not generated by the OSD. But they are included to explain what is happening in the various processing steps.)

In step S130, the cardiac cycles are identified, preferably based on the contours determined in step S120. An adaptive approach may be used in order to keep up with any temporal changes during the monitoring time, such as when the heart rate (HR) increases (e.g., during exertion) or decreases (when the exertion ends). During longer tests, the step of identifying cardiac cycles may be updated periodically (e.g. every 30-60 seconds) and the HR is re-estimated.

In some embodiments, the identification of cardiac cycles without relying on an ECG signal is based on estimating the heart rate (HR) using a Matched Filtering (MF) technique that involves one or more templates of LDS data that correspond to a normal cardiac cycle.

In some preferred embodiments that rely on MF, a pair of templates is used, with one template of the pair being used for slower HRs, and the other template of the pair being used for faster HRs. It is advantageous to use different templates for fast and slow HRs, because the expected features of normal LDS vary as a function of the HR. More specifically, as the heart beats faster, the "A" and "D" features in the LDS (as best seen in FIG. 3A) move towards each other and eventually merge together into what appears to be a single "A" feature.

In these preferred embodiments, the step of identifying the cardiac cycles (i.e., S130) includes two major stages: estimating the HR and match filtering. HR estimation may be implemented, for example, by autocorrelation of the contour of the spectrogram or the raw data. The peaks of the autocorrelation are detected and the average time difference between the peaks is calculated. The reciprocal of the average time is the estimated HR. The variance of the time difference between the peaks is also defined as the HR estimated variability. Once the HR is determined, a template for match filtering is selected based on whether the HR is greater than a threshold rate. A preferred threshold is an HR of 100, in which case one MF template would be selected when the HR is greater than 100 and the other MF template would be selected when the HR is less than 100. The envelope of the LDS is then match-filtered against the selected template. The purpose of this step is detecting the repeatability of a specific selected template. The output of the matched filtering is a continuous signal (or a digital representation thereof), the peak of which represents the start of each cardiac cycle.

Figure 6A:
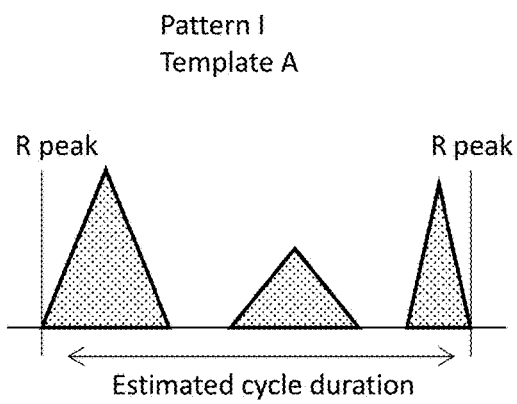
FIGS. 6A and 6B depict a pair of templates used in one preferred embodiment.
Figure 6B:
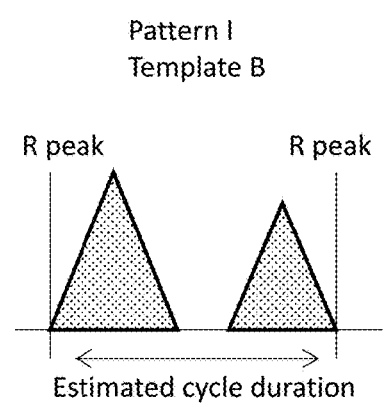
Figure 7A:
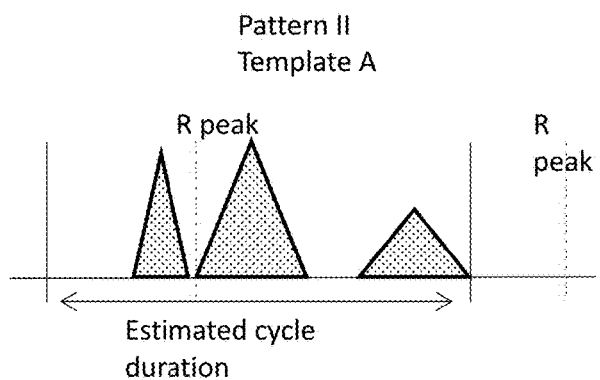
FIGS. 7A and 7B depict a pair of templates used in another preferred embodiment.
Figure 7B:
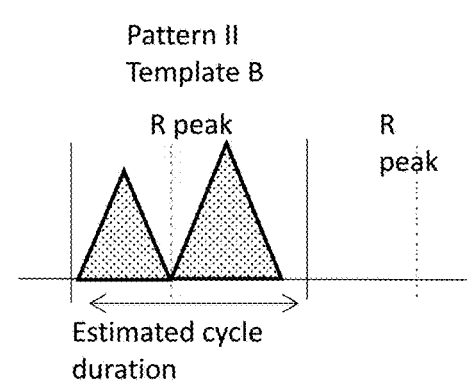

The calculation is conducted in either one of the following two cases: More specifically, when the HR is lower than the threshold, template A is used as the MF kernel, otherwise template B is used. In one preferred embodiment (referred to herein as the Pattern I embodiment), the templates in the pair have the shapes depicted in FIGS. 6A and 6B. In an alternative preferred embodiment (referred to herein as the Pattern II embodiment), the templates in the pair have the shapes depicted in the FIGS. 7A and 7B.

In either scenario, the template is flipped and convoluted with the LDS spectrogram contour or the LDS raw data to calculate the matched filter signal. The peaks of this signal are determined. A single cardiac cycle (i) is represented by a time frame that extends from [detected peak (i) time] and ends in [detected peak (i)+estimated cardiac cycle duration (1/HR)] time.

Alternative approaches for identifying the cardiac cycles may also be used. For example, the contour data that was determined in step 120 may be analyzed to determine the highest velocity that appears in the contour over a given time (e.g., 2 seconds), and the time at which that highest velocity was measured is deemed to be the start of a cardiac cycle. Because the LDS repeats in a periodic manner the vast majority of the time, the next point in time at which that same velocity appears (with a small tolerance of e.g., 5%) is deemed to be the start of the next cardiac cycle.

Figure 8A:
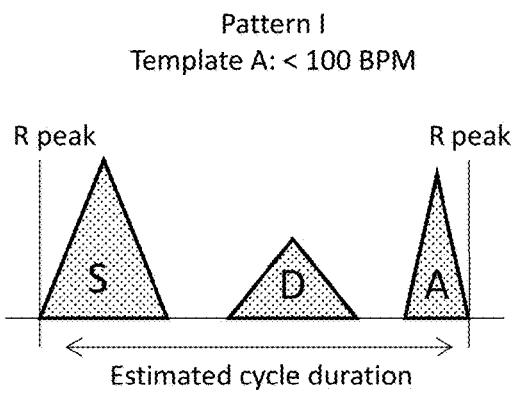
FIGS. 8A and 8B depicts how the A, D, and S features are identified when the FIGS. 6A and 6B templates are used.
Figure 8B:
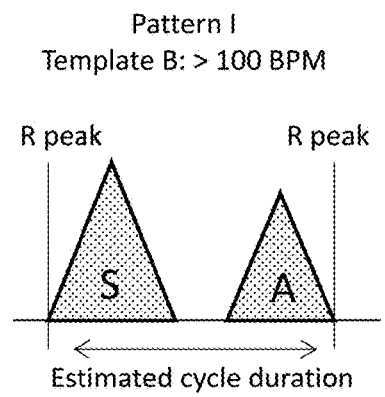

After identification of the cardiac cycles in step S130, processing proceeds to step S140. In step S140, the various features of each cardiac cycle are identified. Note that when two or more DPPC's are available, one of those DPPCs should be selected before the features are extracted. In some preferred embodiments, the identification of features is made based on anatomical, physiological and/or pathological models. In the embodiment that uses Pattern I, the features are identified in two different ways, depending on the HR. More specifically, when the HR is lower than the HR threshold (discussed above); the "S" signal is defined as the signal in the first third of the cardiac cycle, the "D" signal is defined as the signal in the second third of the cardiac cycle, and the "A" signal is defined as the signal in the last third of the cardiac cycle. When the HR is more than the HR threshold; the "S" signal is defined as the signal in the first half of the cardiac cycle, the "A" is defined as the signal in the second half of the cardiac cycle, and the "D" signal is defined as Null. FIGS. 8A and 8B depict these definitions for the Pattern I embodiment.

Figure 9A:
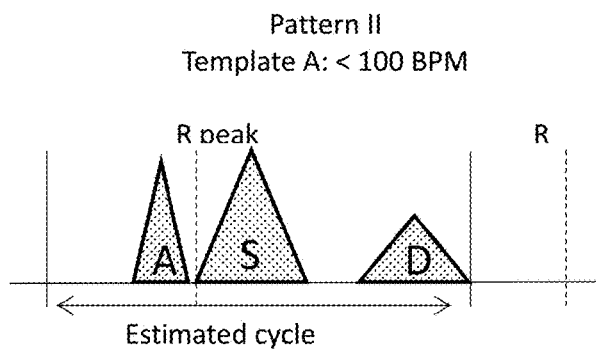
FIGS. 9A and 9B depicts how the A, D, and S features are identified when the FIGS. 7A and 7B templates are used.
Figure 9B:
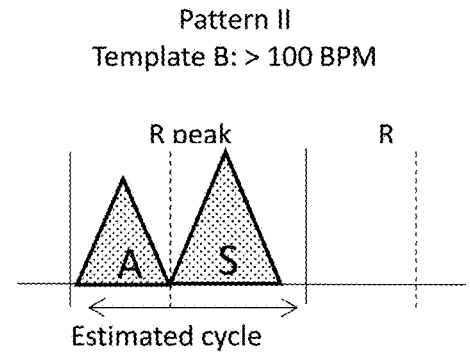

In the alternative embodiment that uses Pattern II, the features are also identified in two different ways, depending on the HR. When the HR is lower than the HR threshold; the "A" signal is defined as the signal in the first third of the cardiac cycle, the "S" signal is defined as the signal in the second third of the cardiac cycle, and the "D" signal is defined as the signal in the last third of the cardiac cycle. When the HR is more than the HR threshold; the "A" signal is defined as the signal in the first half of the cardiac cycle, the "S" is defined as the signal in the second half of the cardiac cycle, and the "D" signal is defined as Null. FIGS. 9A and 9B depict these definitions for the Pattern II embodiment. In alternative embodiments, different approaches may be used to identify the features based on anatomical, physiological and/or pathological models.

After identification of the features in step S140, processing proceeds to step S150. In step S150, characterizations of the A, D, and S features (which were identified in step S140) in are calculated from the LDS. Examples of these characterizations include parameters including but not limited to power integrals, duration, peak velocity, a timing of peak velocity, peak power, a timing of peak power, average velocity, average power, rising slope of a velocity curve, rising slope of a power curve, falling slope of a velocity curve, and falling slope of a power curve. The result of these characterizations will be a set of parameters for each of the features identified in step S140, for each of the cardiac cycles identified in step S130.

After the features have been characterized in the OSD 70, the set of parameters for each of the identified features is transmitted to the remote server 80. But notably, the data at this point is orders of magnitude smaller than the raw ultrasound data that was generated in step S110. In some preferred embodiments, this transmission is implemented via the Internet, via a land-line telephone network, or via a cellular telephone network.

The remaining steps are implemented in the server 80.

In step S200, the set of parameters for each of the identified features for each of the plurality of cardiac cycles is analyzed at the remote server 80 to determine if an abnormality exists in at least one of the plurality of cardiac cycles. Note that when two or more DPPC's are available, the remote server 80 should select the same DPPC that was used by the data reduction processor 70 before this analysis is performed. One example of an algorithm that may be used to determine which cycles are abnormal is to define normal cycles as one of the patterns used above (template A or template B), depending on the HR. All other patterns are defined as "Abnormal" cycles. Optionally, a support-vector-machine (SVM) based classifier may be used to implement this step. In this situation, the SVM is preferably trained offline to differentiate between the two classes; Normal and Abnormal cycles, using its features. The product of the learning (training) stage is a mathematical model which is used online to differentiate (classify) between these classes, optionally using a matched filter. Alternatively or in addition to SVM, machine learning systems (including but not limited to neural networks, deep networks, HMM, etc.) may be used to carry out these steps.

In alternative embodiments, the decision to classify a cycle as abnormal may be based on a set of rules. Examples of rules that may be used to classify a cycle as abnormal include: (a) cycles in which the measured HR differs from an adaptive estimation of HR that is based on the HR of the previous few cycles by an amount that is larger than a threshold (e.g. 20%); (b) If the adaptive HR estimation switches from using pattern A to B, or vice versa; (c) If the estimated HR exceeds an upper threshold (e.g. 120 BPM) or falls below a lower threshold (e.g., 40 BPM); (d) if the features identified in step S140 do not match an expected set of features for a given HR (e.g., if an expected feature is missing, or if an unexpected extra feature is present; or (e) if a characterization of a feature calculated in step S150 has an unexpected value (e.g., if the duration of a feature exceeds an expected value by a threshold percentage). Cycles that do not meet one of the rules for an "abnormal" cycle are classified as normal.

Figure 10A:
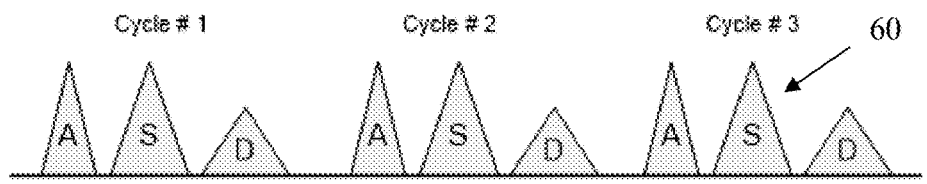
FIG. 10A depicts the set of features that are identified for a normal subject.
Figure 10B:
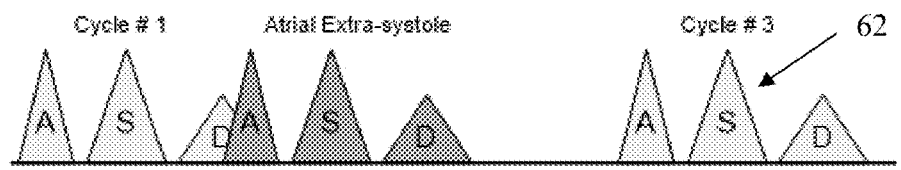
FIG. 10B depicts the set features that are identified in the case of an atrial extra systole.
Figure 10C:
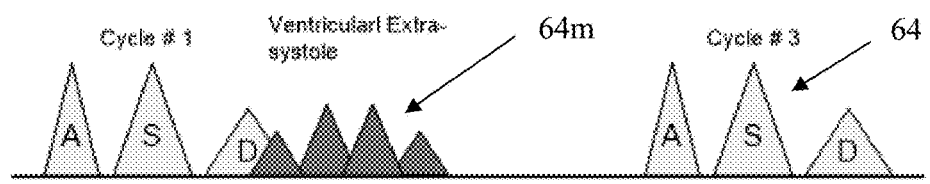
FIG. 10C depicts the set features that are identified in the case of a ventricular extra systole.
Figure 10D:
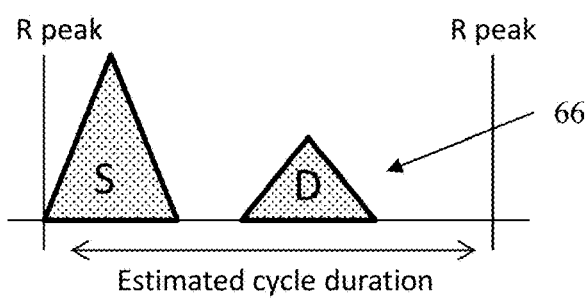
FIG. 10D depicts the set features that are identified in the case of AF.
Figure 10E:
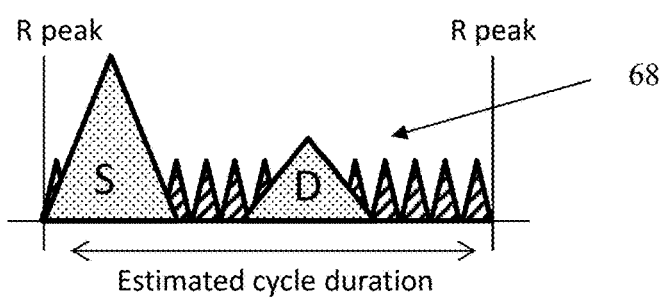
FIG. 10E depicts the set features that are identified in the case of AFT.

In step S210, which is an optional step, the nature of each abnormal cycle is identified. Examples of abnormal cycles include atrial extra systoles, ventricular extra systoles, atrial fibrillation (AF), and atrial flutter (AFT), and expected feature patterns for these four abnormal patterns are depicted in FIGS. 10B-10E, respectively. More specifically, as compared to the expected normal set of features 60 (shown in FIG. 10A), an extra set of discrete "A", "S", and "D" features is present in the case of an atrial extra systole (see the set of features 62 depicted in FIG. 10B). In another example, an extra set of merged features 64*m* is present in the case of a ventricular extra systole (see the set of features 64 depicted in FIG. 10C). In another example, the "A" feature is missing at the end of the cardiac cycle in AF (see the set of features 66 depicted in FIG. 10D). In another example, and a large number of extra "A" features are present in AFT (see the set of features 68 depicted in FIG. 10E). Optionally, within the set of "abnormal" cycles classified previously, the SVM may be used with a different model to identify which of the various abnormalities or arrhythmias is present. Any deviation from the normal expected patterns is recognized. This may be accomplished using an SVM classifier for recognizing AF.

Returning now to FIG. 4, processing continues is step S220, where the remote server outputs an indication to the patient or medical personnel that an abnormal cycle has been detected. If the nature of the abnormal cycles was identified in optional step 180, the output from the remote server preferably specifies the nature of the abnormality. Optionally, an invoice may be sent along with the data output, and the appropriate person is preferably charged for the service by an accounting system.

Example 2

Another example involves diagnosing Congestive Heart Failure (CHF) based on LDS uses the same process described above in connection with FIG. 4. In this particular example, the OSD measurements of LDS are performed in a hospital environment by the Trans-Thoracic Parametric Doppler, TPD, (EchoSense Ltd., Haifa, Israel) that includes a data acquisition signal analysis software (EchoSense Ltd., Haifa, Israel). The raw data from the sensor is processed into sonograms, and if those sonograms are displayed they would resemble the image depicted in the upper panel 50 of FIG. 5. This data is then digitized, processed, and analyzed at the OSD by calculating the contours (i.e., the envelope) of the data from the upper trace. The calculated contour is depicted in the middle trace 52 of FIG. 5. Next, the cardiac cycles are identified. Next, the minima and maxima of this contour are extracted so as to define the different individual LDS signals, S, D and A, as described in Palti Y, Kanter A, Solter E, Schatzberger R, Kronzon I. Pulmonary Doppler signals: a potentially new diagnostic tool. Eur J Echocardiogr 2011; 12 (12):940-944 and Palti Y., Schatzberger R., Zreik M., Solter E. and Kronzon I. Footprints of Cardiac Mechanical Activity as Expressed in Lung Doppler Signals. Echocardiography (2015):407-410. The features of each of the S, D, and A signals in each cardiac cycle are then characterized into parameters. Examples of the characteristics include power integrals, duration, peak velocity, a timing of peak velocity, peak power, a timing of peak power, average velocity, average power, rising slope of a velocity curve, rising slope of a power curve, falling slope of a velocity curve, and falling slope of a power curve, as well as presence of signal splitting, ratios and other relationships between the different features and averages of all the above over a selected string of cardiac cycles. The above process reduces the amount of data that is needed to evaluate the health of the patient drastically (e.g., on the order of 1:10,000).

Figure 11:
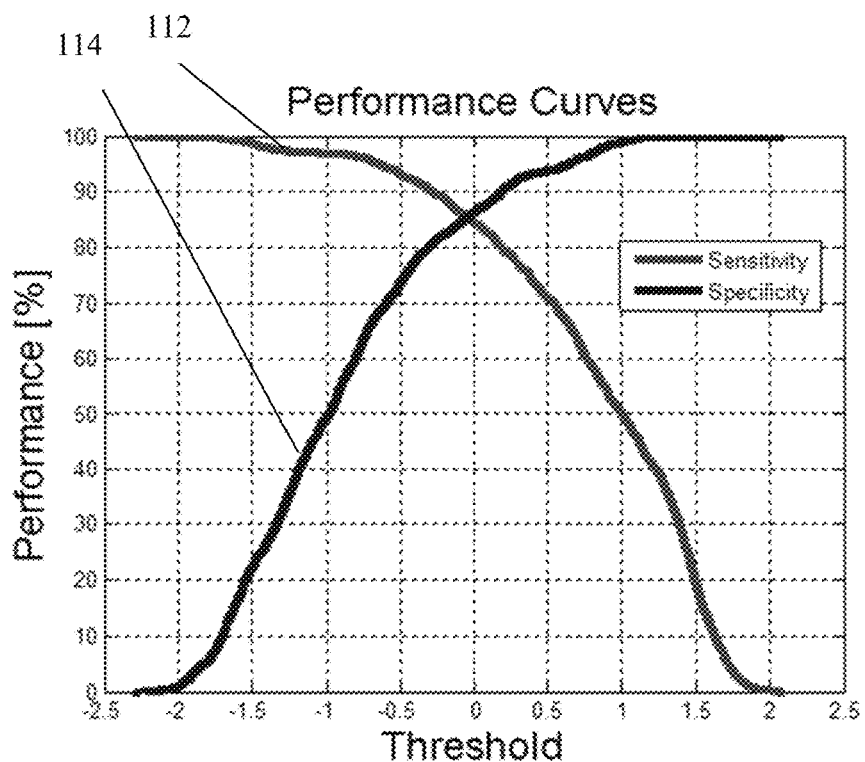
FIG. 11 is a set of performance curves for the second example.

The parameters for each of the S, D, and A signals in each cardiac cycle are then coded and transmitted to the server 80 (shown in FIG. 1). Optionally, patient information (e.g., age, health history, family history, etc.) is also transmitted to the server 80. The server 80 performs classification using a classification program and algorithms that match the ones used in the feature extraction DPPC process, i.e. following the physio-pathological model. The classification may include the construction of Performance Curves, ROC curves and the determination of classification (diagnosis) success as expressed in the sensitivity curve 112 and the specificity curve 114 depicted in FIG. 11. For the particular example described, an accuracy of 85.4%, a specificity of 86.2%, and a sensitivity of 84.6% was achieved. The server 80 then identifies the nature of any abnormal cycles to determine a diagnosis and transmits a response to the clinic, health care provider, or the patient. In the preferred process the results of the classification, etc. and diagnoses are transmitted to its destination within a few seconds. To achieve this the server 80 (e.g., a cloud-base server) may activate numerous processors in parallel. Preferably the server 80 is designed to handle numerous sites at the same time.

Final results of the Feature analysis, the conclusions and recommendations are prepared together with the corresponding invoices and transmitted to the relevant destination. Optionally, a payment transaction may be processed via a credit card, PayPal, or other payment mode that was approved by the customer.

Example 3

A third example involves diagnosing Pulmonary Hypertension (PH) based on LDS using the same process described above in connection with FIG. 4. LDS recordings were made over 5 locations on the right chest wall at intercostal spaces (ICS) 2 to 6, on patients in a sitting or semi-reclining position. Recording duration at each point was about 1 minute. The transducer was positioned at an angle close to 90° with respect to the chest surface, 5-6 cm to the right of the mid-sternal line. Standard gel was used for contact. ECG (lead 1) was concomitantly recorded. Measurements were carried out by three technicians trained to use the system.

The recorded lung Doppler signals were processed by a specialized signal processing software (Echosense Ltd, Haifa, Israel) that runs in the data reduction processor 70. The spectrograms of both velocity and the reflected ultrasound power were analyzed in the data reduction processor 70 to identify the cardiac cycles, identify features in each cardiac cycle, and characterize the features into parameters for characteristics related to timing, peak values, slopes, duration, integral of reflected power, etc. This step is similar to Example 2 described above in which the characteristics or features of each cardiac cycle (e.g., the S, D, and A signals in each cardiac cycle) are determined. Examples of the characteristics include power integrals, duration, peak velocity, a timing of peak velocity, peak power, a timing of peak power, average velocity, average power, rising slope of a velocity curve, rising slope of a power curve, falling slope of a velocity curve, and falling slope of a power curve, as well as the presence of signal splitting, ratios and other relationships between the different features.

Figure 12:
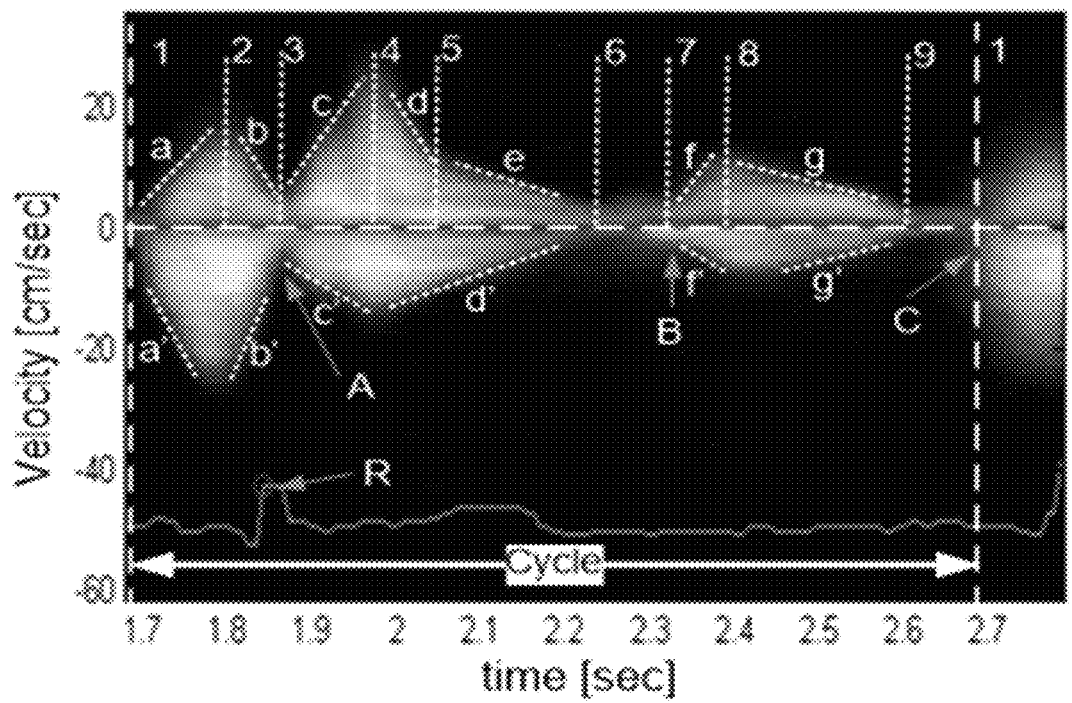
FIG. 12 depicts a display of the LDS averaged over 20 cycles for the third example.

FIG. 12 depicts a display of the LDS averaged over 20 cycles, which shows the averaged single cycle LDS recorded from a subject with a normal cardio-pulmonary system using the TPD. The main Markers used to automatically define the features, as extracted by the TPD data analysis software (which runs in the data reduction processor 70) are depicted in FIG. 12.

The parameters that characterize each of the features (e.g., the S, D, and A signals) in each cardiac cycle that were determined in the data reduction processor 70 are then transmitted to the remote server 80, and the server receives this data.

Prior to receipt of this data (e.g., days or weeks in advance), the server 80 has been pre-programmed to perform classification using a support vector machine (SVM). In some preferred embodiments, the server has pre-programmed using a machine-learning methodology for separation of PH from non-PH patients, and PH from controls. SVM is a widely employed method including in medicine and medical research.

Two approaches for pre-programming the server 80 to implement classification are explained below, but other approaches may also be used. In Approach 1, The k-fold cross validation (CV) method used to evaluate the SVM classification performance. In such cross validation, patients and controls or patients and non-PH are divided into k sub-groups of equal number. The classifier is trained on all except one sub-group and the results are validated on the excluded sub-group. This process is iterated k times and repeated n times.

Approach 2 uses a training & test subgroup approach, which is the standard machine learning mode of statistical analysis. Within this framework, all groups/subgroups consisted of a similar number of PH and Non-PH or control subjects. Each training subgroup consisted of approximately ⅔ of the total (53/79) number of subjects in each group, while the test subgroups consisted of the rest of the subjects. Each sub-group was used to separately train the SVM classifier. Following training the "educated" system was used as a classifier of the test group and its success was registered. In general, the first approach (CV), is used when the number of subjects is too small to obtain a statistically significant result using the Training & Test methodology. As the number subjects grows, the results obtained by the two approaches converge.

The following section shows that a server 80 can be successfully pre-programmed to recognize PH. Statistical analysis is used to determine the probability that two groups are different. A Student's t test was performed. All p values were two-sided, and p values less than 0.05 were considered to indicate statistical significance. The TPD performance results reported here are the averages of n=20 repetitions of the k=10-fold cross validation process. The 95% confidence intervals of the TPD performance measures were derived on the basis of the standard deviation of these measures over the 20 repetitions. Calculations were performed by Matlab version R2012b and Microsoft Excel 2010.

The results of the clinical characteristics of the study population are reported in Table 1. The TPD performance in detecting PH vs. non-PH or Controls, using approach 1 is given in Table 1, together with their 95% confidence intervals.

Figure 13A:
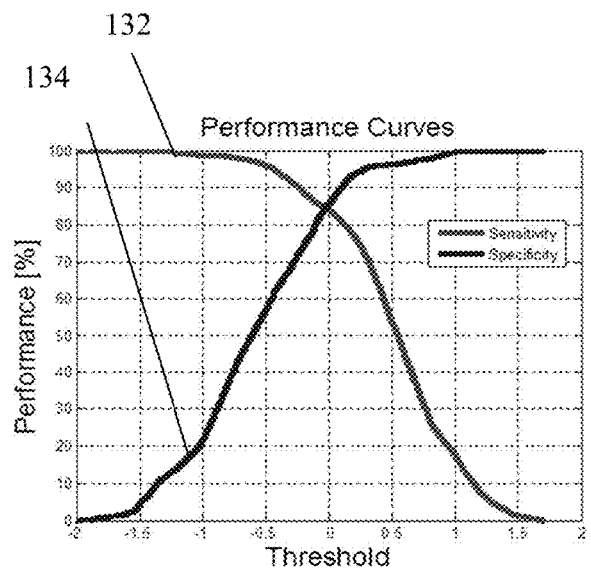
FIGS. 13A and 13B are, respectively, sensitivity/specificity and ROC curves for the third example.
Figure 13B:
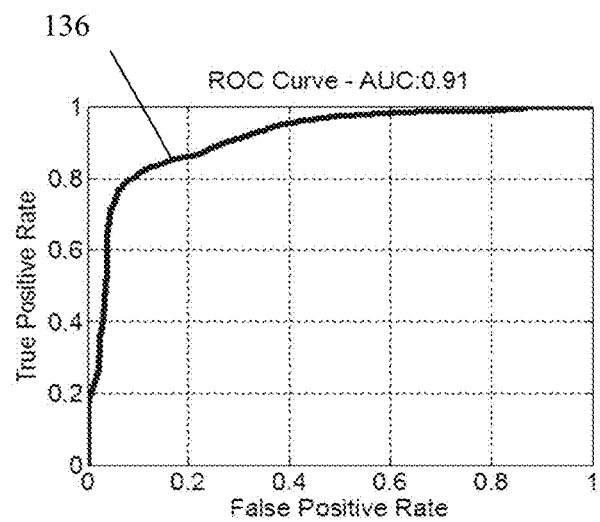

Sensitivity/specificity and ROC curves for the PH vs. non-PH are presented in FIGS. 13A and 13B respectively. More specifically, the performance curves obtained for all groups are presented in FIG. 13A (which shows the sensitivity curve 132 and specificity curve 134 for PH detection by the TPD approach 1) and FIG. 13B (which shows the true positive rate curve 136 for the Receiver operator curve (ROC) approach 1. The area under the curve 136 in FIG. 13B is 0.91. The corresponding curves for the PH vs. control were very similar. Note that the TPD detection rates were similar across all 3 operators and 4 clinical sites.

TABLE 1

Performance measures for PH vs. non-PH & vs. healthy controls by the TPD, Approach 1.

| Performance Measure | PH vs. non-PH | | PH vs. healthy control | |
|---|---|---|---|---|
| | Result (%) | 95% CI | Result (%) | 95% CI |
| Accuracy | 84.80% | [83.3-86.3] | 85% | [83.8-86.2] |
| Sensitivity | 83.90% | [82.3-85.5] | 82.70% | [81.3-84.1] |
| Specificity | 85.70% | [83.9-87.5] | 87.40% | [86.3-88.5] |

The PH etiology is presented in Table 2. Among the 79 PH patients that underwent RHC, in 64 (81%) the etiology was pre-capillary (mean pulmonary capillary wedge pressure, mPCWP≤15 mmHg), in 12 (15%) it was post-capillary (mPCWP>15 mmHg) and in 3 (4%) it was undetermined as it was impossible to obtain reliable PCWP. The success rate for PH detection with LDS for each group is given in Table 2.

TABLE 2

Etiology of PH, according to the Nice 2013 classification

| Cause [Nice classification] | Number of Patients (%) | PH Detection rate in 79PH/79non-PH |
|---|---|---|
| Pulmonary arterial hypertension [1] | 31 (39%) | 27 (87%) |
| Left heart disease [2] | 12 (16%) | 11 (92%) |
| Pulmonary disease [3] | 5 (6%) | 4 (80%) |
| Chronic thromboembolic pulmonary hypertension [4] | 23 (29%) | 17 (74%) |
| Multifactorial [5] | 5 (6%) | 5 (100%) |
| Not classified | 3 (4%) | 2 (67%) |

For the Main Classification Features, The LDS features that carried the highest predictive value for selection of PH vs. non-PH and PH vs. control are given in Table 3:

TABLE 3

Average Feature values that contain the highest classification power (S systolic component, D diastolic component, A atrial contraction component)

| Signal type | Feature | PH | Control | Feature | PH | Non-PH | Marked in FIG. 12 as: |
|---|---|---|---|---|---|---|---|
| S | Peak Velocity (cm/s) | −10.5 | −16 | Peak Velocity (cm/s) | −10.5 | −16.9 | Velocity at 4 |
|   | Rise slope (cm/s$^2$) | 131.2 | 281.4 | Rise slope (cm/s$^2$) | 158.3 | 230.5 | c |
|   | Peak velocity Time (as fraction of RR interval) | 0.15 | 0.1 |   |   |   | (4 to R)/(R-R) |
| D | Peak Velocity (cm/s) | 6.8 | 9.5 | Peak Velocity (cm/s) | 6.8 | 9.3 | Velocity at 8 |
|   |   |   |   | Weighted velocity (cm/s) | 7.2 | 10.4 |   |
| A | Rise slope (cm/s$^2$) | 77.4 | 126.7 |   |   |   | a |

It is seen that signals S & D carry most information and that both show similar differences in the corresponding features.

Figure 14:
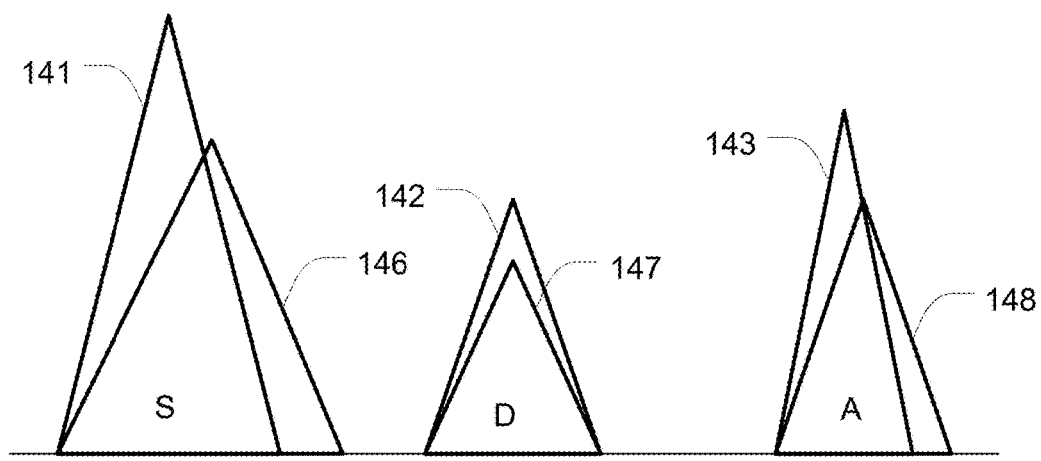
FIG. 14 depicts the difference in shape of the LDS for PH and non-PH patients.

FIG. 14 is a schematic presentation of the shape of LDS velocity signals for PH and non-PH patients. The features 141-143 (i.e., the taller triangles) represents control subjects and the features 146-148 (i.e., the shorter triangles) represents PH patients. This figure compares schematically the typical shape of signals S, D and A in control patients with those of PH patients, as presented in Table 3. This figure also illustrates the fact that in patients with PH the systolic signal (S) 146 has lower velocity, slower slope and a delayed peak as compared to the corresponding feature 141 for a control patient; the diastolic feature (D) 147 for the PH patient is of slower velocity than the corresponding feature 142 for a control patient; and the atrial contraction feature (A) 148 for the PH patient has lower velocity, slower slope and a slightly delayed peak than the corresponding feature 143 for a control patient.

As explained above, the server 80 receives parameters that characterize each of the features (e.g., the S, D, and A signals) in each cardiac cycle that were determined in the data reduction processor 70. Based on these parameters, the server 80 makes a determination if the patient has PH by analyzing the parameters to identify abnormal cycles that indicate PH. In cases where the server 80 has been pre-programmed to perform classification using SVM, the server will rely on the previous learning session to distinguish between PH and non-PH by examining the received characteristics of the various features. In other embodiments, alternative approaches for distinguishing between PH and non-PH may be applied. The server 80 makes a determination regarding PH and prepares an appropriate report, which is transmitted to the clinic, health care provider, and/or the patient. Optionally, corresponding invoices are transmitted to the relevant destination. Optionally, a payment transaction may be processed via a credit card, PayPal, or other payment mode that was approved by the customer.

While the present invention has been disclosed with reference to certain embodiments, numerous modifications, alterations, and changes to the described embodiments are possible without departing from the sphere and scope of the present invention, and the present invention is not limited to the described embodiments.

I claim:

1. A method of analyzing health of a subject, the method comprising the steps of:

transmitting ultrasound energy into a lung of the subject;

receiving ultrasound energy reflected from the lung of the subject and detecting Doppler shifts in the reflected ultrasound energy;

processing the Doppler shifts into power and velocity data;

identifying a plurality of cardiac cycles within the power and velocity data;

identifying a plurality of ultrasound power and velocity features of the power and velocity data corresponding to each of the plurality of cardiac cycles;

characterizing each of the identified ultrasound power and velocity features that correspond to cardiac cycles into a set of parameters;

transmitting the set of parameters for each of the identified ultrasound power and velocity features that correspond to cardiac cycles to a remote location;

analyzing the set of parameters for each of the identified ultrasound power and velocity features for each of the plurality of cardiac cycles at the remote location to determine if an abnormality exists in at least one of the plurality of cardiac cycles; and if it is determined in the analyzing step that an abnormality exists in at least one of the plurality of cardiac cycles, outputting an indication from the remote location that the abnormality exists.

2. The method of claim 1, wherein the step of processing the Doppler shifts into power and velocity data includes processing the Doppler shifts using at least an algorithm designed to increase signal from moving borders between blood vessels in the lung and air filled alveoli that surround the blood vessels, with respect to other reflected ultrasound energy.

3. The method of claim 1, wherein the step of identifying cardiac cycles comprises the steps of:
   determining an envelope of the power and velocity data; and
   identifying cardiac cycles based on the determined envelope.

4. The method of claim 1, wherein the set of parameters for each of the identified ultrasound power and velocity features that correspond to cardiac cycles comprises at least two of: a power integral, duration, peak velocity, a timing of peak velocity, peak power, a timing of peak power, average velocity, average power, rising slope of a velocity curve, rising slope of a power curve, falling slope of a velocity curve, falling slope of a power curve.

5. The method of claim 1, wherein the set of parameters for each of the identified ultrasound power and velocity features that correspond to cardiac cycles comprises at least peak velocity and a timing of peak velocity.

6. The method of claim 1, wherein the indication from the remote location that the abnormality exists specifies a nature of the abnormality.

7. The method of claim 1, wherein the step of analyzing the set of parameters comprises detecting when (a) a peak velocity of a systolic feature is lower than expected for healthy subjects, (b) the peak velocity of the systolic feature arrives later than expected for healthy subjects, (c) a peak velocity of an atrial feature is lower than expected for healthy subjects, and (d) the peak velocity of the atrial feature arrives later than expected for healthy subjects, and
   wherein the indication from the remote location that the abnormality exists specifies that the abnormality is pulmonary hypertension.

8. The method of claim 1, wherein the step of analyzing the set of parameters comprises detecting when an extra systolic feature, an extra diastolic feature, and an extra atrial feature appear within a given cardiac cycle, and
   wherein the indication from the remote location that the abnormality exists specifies that the abnormality is atrial extra systole of sinus origin.

9. The method of claim 1, wherein the step of analyzing the set of parameters comprises detecting when a plurality of extra atrial features appears within a given cardiac cycle, and
   wherein the indication from the remote location that the abnormality exists specifies that the abnormality is atrial flutter.

10. The method of claim 1, wherein the step of analyzing the set of parameters comprises detecting when an atrial feature is missing from a given cardiac cycle, and
    wherein the indication from the remote location that the abnormality exists specifies that the abnormality is atrial fibrillation.

11. The method of claim 1, wherein the step of analyzing comprises performing classification using a support vector machine.

12. The method of claim 1, wherein the step of transmitting the set of parameters for each of the identified features to a remote location comprises transmitting data via the Internet.

13. The method of claim 1, wherein the step of transmitting the set of parameters for each of the identified features to a remote location comprises transmitting data via a telephone network.

14. A system for analyzing health of a subject, the system comprising:
    an ultrasound transducer located at a first location and configured to transmit ultrasound energy into a lung of the subject and receive ultrasound energy reflected from the lung of the subject;
    an ultrasound processor located at the first location and configured to detect Doppler shifts in the reflected ultrasound energy and process the Doppler shifts into power and velocity data;
    a first processor located at the first location and configured to identify a plurality of cardiac cycles within the power and velocity data, identify a plurality of ultrasound power and velocity features of the power and velocity data corresponding to each of the plurality of cardiac cycles, characterize each of the identified ultrasound power and velocity features that correspond to cardiac cycles into a set of parameters, and transmit the set of parameters for each of the identified ultrasound power and velocity features that correspond to cardiac cycles to a second location that is remote from the first location; and
    a second processor located at the second location, wherein the second processor is configured to (a) analyze the set of parameters for each of the identified ultrasound power and velocity features for each of the plurality of cardiac cycles to determine if an abnormality exists in at least one of the plurality of cardiac cycles, and, (b) if it is determined that an abnormality exists in at least one of the plurality of cardiac cycles, output an indication that the abnormality exists.

* * * * *